(12) United States Patent
Tsuruda et al.

(10) Patent No.: US 6,924,410 B2
(45) Date of Patent: Aug. 2, 2005

(54) ULTRAVIOLET-SCREENING PATCH

(75) Inventors: Kiyomi Tsuruda, Tosu (JP); Yasuhiro Ikeura, Tosu (JP)

(73) Assignee: Hisamitsu Pharmaceutical Co., Ltd., Tosu (JP)

( * ) Notice: Subject to any disclaimer, the term of this patent is extended or adjusted under 35 U.S.C. 154(b) by 112 days.

(21) Appl. No.: 10/221,848

(22) PCT Filed: Mar. 13, 2001

(86) PCT No.: PCT/JO01/01978

§ 371 (c)(1),
(2), (4) Date: Sep. 16, 2002

(87) PCT Pub. No.: WO01/68061

PCT Pub. Date: Sep. 20, 2001

(65) Prior Publication Data

US 2003/0149385 A1 Aug. 7, 2003

(30) Foreign Application Priority Data

Mar. 17, 2000 (JP) ........................................ 2000-075554

(51) Int. Cl.[7] .............................................. A61F 13/00

(52) U.S. Cl. ........................ 602/48; 424/443; 424/447; 424/449; 604/304

(58) Field of Search .............................. 602/41–59, 43; 424/443–449; 604/304–308

(56) References Cited

U.S. PATENT DOCUMENTS 6,241,998 B1 * 6/2001 Muchin ....................... 424/448

FOREIGN PATENT DOCUMENTS

JP       530118 U   * 4/1993
JP       10265371 A * 10/1998 .......... A61K/09/70

* cited by examiner

*Primary Examiner*—Kim M. Lewis
(74) *Attorney, Agent, or Firm*—Kubovcik & Kubovcik

(57) ABSTRACT

A patch has a backing which has been subjected to an ultraviolet-screening processing, the backing usually being of one layer. The ultraviolet-screening processing usually uses an organic ultraviolet absorbent and/or an inorganic ultraviolet-screening agent. The patch can contain in its base a medicine of poor photo-stability and a non-steroidal anti-inflammatory analgesic.

11 Claims, 1 Drawing Sheet

ULTRAVIOLET-SCREENING PATCH

TECHNICAL FIELD

The present invention relates to a patch which contains a medicine improved in photostability.

BACKGROUND ART

Pharmaceutical preparations that have been so far used for percutaneous administration of medicaments have dosage forms of ointment, gel, lotion, and the like. Recently, however, a patch, which is also called a tape-aid (patch) or a gel patch (cataplasm), has been practically used and noted, because it can quantitatively administer medicaments and can be peeled off at any time when it has induced any side effects. Such a patch includes a local preparation containing a non-steroidal drug aimed at anti-inflammatory analgesic effects or a systemic preparation containing a nitric acid ester aimed at remedying circulatory diseases or containing a female hormone aimed at remedying climacteric disturbance or osteoporosis.

On the other hand, there have arisen such a problem that, when these patches are applied, ultraviolet rays from the sun decompose the drug contained in the base thereof to lower the content and thus does not allow the drug to exhibit its original efficacy and another problem that the photolyzed products induce an allergy to bring about adverse effects.

For inhibiting the influence of the ultraviolet light of the sun, Japanese Pat. Publn. No. Hei 5-8169 (No.8169/1993) discloses an external preparation in which an effective ingredient is prevented from photolysis by incorporated with an ultraviolet absorbent in the base of the preparation. Further, Japanese Pat. Appln. Laid-Open Gazette No. Hei 10-265371 (No.256371/1998) discloses a percutaneously absorbable patch having as a backing a laminate composed of two or more layers, in which at least one layer of said laminate is a resin film containing an ultraviolet absorbent.

As described above, the means for keeping the stability of a medicine in patches has generally been to incorporate an ultraviolet absorbent into the base, but there has remained a problem to be worried about as to safety and the like due to said absorbent's direct contact with or absorption into the skin. On the other hand, the patch whose backing, which will be directly exposed to the ultraviolet rays of sun, is made of a laminate comprising two or more layers for screening the ultraviolet requires troublesome manufacturing steps for laminating the backing and also involves high costs.

The present invention has been made for solving the above problems, and an object thereof is to provide a patch excellent in securing therapeutic effects and in safety for the skin by improving the photostability of a medicine with a backing composed of a single layer.

DISCLOSURE OF THE INVENTION

The present inventors have made intensive studies in an attempt to achieve the above object and, as a result of their studies, have found that processing a single-layer backing of a patch in order to screen or shield ultraviolet light protects the skin, namely, the region to be patched against the influence of the ultraviolet light as well as remarkably inhibits the decomposition of a medicine with ultraviolet light if such a medicine is contained in the base of the patch. Employment of a backing which either an organic ultraviolet absorbent has been attached to, absorbed in or fixed to or an inorganic ultraviolet-screening agent has been added to or kneaded in, prevents the ingredients of an adhesive base from oozing out between the base and the backing and also from deeply permeating inside the backing. In other words, the present inventors have found that without adding such a stabilizer as an ultraviolet absorbent into the base or without making a backing out of plural layers as conventionally done, lowering of the medicine content by photolysis and the incidence of a new skin allergy due to the photolytes can be avoided by making full use of the functions of the single-layer backing. The present invention has thus been accomplished.

Accordingly, the patch of the present invention has a single-layer backing which has been subjected to an ultraviolet-screening processing. The patch herein includes an adhesive plaster, a tape-aid for wounds, a plaster (tape-aid or patch), a poultice (gel patch), reservoir-type patch, cosmetic pack sheet and a taping preparation.

Practical Embodiments of the invention will be explained below.

In the ultraviolet-screening processing of the backing according to the present invention, an organic ultraviolet absorbent and/or inorganic ultraviolet-screening agent can be used. The organic ultraviolet absorbent is preferably one or more members selected from benzotriazole derivatives, p-aminobenzoic acid derivatives, anthranilic acid derivatives, salicylic acid derivatives, cinnamic acid derivatives, benzophenone derivatives, coumalic acid derivatives, cyanoacrylate derivatives and amino acid-based compounds.

The inorganic ultraviolet-screening agent is preferably one or more members selected from titanium oxide, zinc oxide, ferric oxide, talc, kaolin, alumina and calcium carbonate.

The patch of the present invention can contain a medicine poor in photostablity. Thus, the backing processed for screening ultraviolet is particularly effective for less photostable medicines.

The patch of the present invention may contain a non-steroidal anti-inflammatory analgesic, which includes ketoprofen, diclofenac, suprofen, piroxicam, indomethacin, flurbiprofen, felbinac, loxoprofen or their salts.

The organic ultraviolet absorbents used in the present invention more specifically include the following compounds.

The benzotriazole derivatives include 2-(2'-hydroxy-5'-tert-methylphenyl)benzotriazole, 2-(2'-hydroxy-5'-tert-butylphenyl)benzotriazole, 2-(2'-hydroxy-3',5'-di-tert-butylphenyl)benzotriazole, 2-(2'-hydroxy-3'-tert-butyl-5'-methylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-amylphenyl)benzotriazole, 2-[2'-hydroxy-3'-(3",4",5",6"-tetrahydrophthalimidomethyl)-5'-methylphenyl]-benzotriazole,2,2-methylenebis[4-(1,1,3,3-tetramethylbutyl)-6-(2H-benzotriazole-2-yl)phenol], and 2-(2'-hydroxy-5'-meth-acryloxyphenyl)-2H-benzotriazole.

The p-aminobenzoic acid derivatives include esters of p-aminobenzoic acid with ethyl, propyl, butyl, isobutyl, monoglyceride, etc., p-dimethylaminobenzoic acid and esters thereof with ethyl, amyl, etc., p-diethylaminobenzoic acid and esters thereof with ethyl, amyl, etc., and 2-ethylhexyl p-dimethylaminobenzoate.

The anthranilic acid derivatives include anthraniliates and, particularly, menthyl anthranilate among them.

The salicylic acid derivatives preferably include salicylates, among them more preferred are phenyl salicylate, p-tert-butylphenyl salicylate, p-octylphenyl salicylate, 2-ethylhexyl salicylate, homomenthyl salicylate and other esters of salicylic acid with ethylene glycol, glycerin, etc., as well as salicylic acid triethanol ammonium salt.

The cinnamic acid derivatives illustratively include cinoxate, diethanolamine p-methoxycinnamate, 2-ethylhexyl p-methoxycinnamate and isopropyl p-acetamido-cinnamate.

The benzophenone derivatives illustratively include 2,4-dihydroxybenzophenone, 2-hydroxy-4-methoxybenzophenone, 2-hydroxy-4-n-octoxybenzophenone, 2-hydroxy-4-dodecyl-oxybenzophenone, 2,2'-dihydroxy-4-methoxybenzophenone, 2,2'-dihydroxy-4,4'-dimethoxybenzophenone, 2-hydroxy-4-methoxybenzophenone-5-sulfonic acid, 4-phenylbenzophenone-2-carboyxlic acid isooctyl ester, 2-hydroxybenzophenone, and 2,2',4,4'-tetrahydroxybenzophenone.

The coumalic acid derivatives illustratively include 7-ethylamino-4-methylcoumarin, 7,8-dihydroxycoumarin, 6,7-dihydroxycoumarin, 7-hydroxycoumarin and 4-methyl-7-hydroxycoumarin.

The cyanoacrylate derivatives illustratively include 2-ethylhexyl 2-cyano-3,3'-diphenylacrylate and ethyl 2-cyano-3,3'-diphenylacrylate.

The amino acid compounds illustratively include urocanic acid, tributamine derivatives and glutamic acid derivatives.

Other organic ultraviolet absorbents illustratively include imidazoline derivatives, pyrimidine derivatives, tetrazole derivatives, dioxane derivatives, furan derivatives, piron derivatives, camphor derivatives, nucleic acid derivatives, allantoin derivatives, nicotinic acid derivatives, shikonin and vitamin $B_6$ derivatives.

The processing for ultraviolet screening with these organic ultraviolet absorbents includes a process wherein the absorbents are attached to, absorbed in or fixed to fibers or cloth which are materials for a single-layer backing for patch.

These organic ultraviolet absorbents may be used singly or in a combination of two or more members thereof for the single-layer backing, and the amount thereof used is preferably 0.01–20% by mass, more preferably 0.05–5% by mass, based on the mass of the whole backing including the absorbent(s). Such mixing ratios will result in screening ultraviolet light so sufficiently that the resultant patch is improved in the photostability of a medicine and also highly improved in skin safety.

If the amount of the organic ultraviolet absorbent used is less than 0.01% by mass, the ultraviolet light, on the contrary, will not be sufficiently screened unfavorably. More than 20% by mass of the absorbent cannot be fixed in the backing to unfavorably move into the base or bleed onto the surface of the backing.

The inorganic ultraviolet-screening agents illustratively include titanium oxide, zinc oxide, ferric oxide, talc, kaolin, alumina and calcium carbonate, and one or more members selected therefrom can be contained in the backing.

The processing for ultraviolet screening with the inorganic ultraviolet-screening agent is carried out by adding or kneading the inorganic ultraviolet-screening agent into a polymer for modification during a step of manufacturing fibers (step of polymerization and spinning) which will be a material for the backing. Then, the modified polymer is made into fibers which serve as a material for the single-layer backing.

The amount of the inorganic ultraviolet-screening agent used is preferably 0.1–20% by mass, more preferably 0.5–10% by mass, based on the mass of the whole backing containing the screening agent. Such mixing ratios will enable the resulting backing to exhibit a sufficient screening effect against the ultraviolet light. If the amount of the screening agent is less than 0.1% by mass, the ultraviolet light will not sufficiently screened unfavorably. More than 20% by mass of the screening agent is not preferable, because such amounts will not disperse uniformly in a polymer for the backing during the steps of making the polymer into fibers, and the resulting fibers will fluff, break or have stripers.

The single-layer backing can further be improved in ultraviolet-screening effect if it contains both the organic ultraviolet absorbent and the inorganic ultraviolet-screening agent. A composite of a backing containing the organic ultraviolet absorbent and another backing containing the inorganic ultraviolet-screening agent can also be used. The single-layer backing according to this invention which has been subjected to the special processing with the organic ultraviolet absorbent and/or inorganic ultraviolet-screening agent has a light transmittance of preferably not more than 26%, more preferably not more than 20%, further more preferably not more than 15% under the condition of an ultraviolet intensity being about 0.14 mW/hr/cm$^2$ and at a temperature of 25° C. In addition, because the organic ultraviolet absorbent and/or the inorganic ultraviolet-screening agent are formed in or on the backing by the aforementioned means, the ingredients, inclusive of adhesives, medicinal ingredients and other additives, of an adhesive base are prevented from oozing from between the base and the backing and also prevented from permeating deeply inside the backing. Further, the backing processed for screening the ultraviolet as above has a strengthened adhesive power between the surface thereof and the adhesive base.

The material for the backing to be used for the patch of the present invention is not particularly limited and illustratively includes polyethylene, polypropylene, polybutadiene, polyester, nylon, polyurethane, polyvinyl chloride, wool, rayon and cotton. These can be processed into a fabric, knit, non-woven fabric, film or the like and then used as a backing. In particular, a stretchable backing is preferred.

The patch of the present invention may contain one or more medicines. The medicines are not limited and illustratively include narcotic analgesics (e.g. morphine hydrochloride, codeine phosphate), non-narcotic analgesics (e.g. fentanyl citrate), adrenal cortex hormones (e.g. hydrocortisone, hydrocortisone acetate, dexamethasone, dexamethasone acetate, predonisolone, predonisolone acetate, clobetasone butyrate, fluocinolone acetonide, deprodon propionate, betamethasone, fluocinonide), anti-histamines (e.g. diphenhydramine hydrochloride, chlorphenylamine maleate, isotibenzyl hydrochloride, mequitazine, promethazine hydrochloride, cyproheptadine hydrochloride), fungicides (e.g. miconazole nitrate, miconazole hydrochloride, clonazole hydrochloride, iconazole nitrate, econazole Nitto, oxiconazole nitrate, sulconazole nitrate, lanaconazole, terbinafin hydrochloride, amorphine nitrate, bifonazole, tolnaftate, clotrimazole, butenafin hydrochloride), topical anesthetics (e.g. dibucaine hydrochloride, lidocaine, lidocaine hydrochloride, tetracaine hydrochloride, procaine hydrochloride), β-blockers (e.g. propranolol hydrochloride, pindolol, carteolol hydrochloride, timolol maleate), vasodilators (e.g. nitroglycerin, isosorbide dinitrate, nifedipine, dilthiazem hydrochloride, dipyridamole), anti-allergic agents (e.g. salbutamol hydrochloride, procaterol hydrochloride, sodium clomoglyeate, tranilast, ketotifen fumarate, azelastine hydrochloride), additionally arthrifuges/drugs against hyperuricemia, pituitary hormones, sex hormones, prostaglandins, anesthetics, vitamines, etc. Of these medicines, the backing according to the present invention have the ultraviolet-screening effect on medicines of poor photostability, particularly including non-steroidal anti-inflammatory analgesics such as ketoprofen, diclofenac, suprofen, piroxicam, indomethacin, flurbiprofen, felbinac, loxoprofen, ibuprofen, ketorolac, naproxen, benoxaprofen, carprofen and fenoprofen as well as their medically acceptable inorganic or organic salts. Of these non-steroidal anti-inflammatory analgesics, ketoprofen is most preferable. The mixing ratio of the medicine to the total amount of the base containing said medicine is preferably 0.01–30% by mass, more preferably 0.1–16% by mass. Sufficient pharmacological effect can be expected with this mixing ratio. In particular, the mixing ratio of the non-steroidal anti-inflammatory analgesic in the base to the total amount of the base is preferably 0.1–7.0% by mass, more preferably 0.3–5% by mass.

A cosmetic pack sheet, which is one embodiment of the patch of the present invention, is used mainly for the purpose of skin beauty. For the sake of accelerating the skin beauty, the sheet may contain one or more members selected from vitamin C, fruit juice extract containing it (e.g. rosa fruits extract, orange extract, orange juice, raspberry extract, cucumber extract, gardenia extract, grape fruit extract, haw extract, Japanese pepper extract, hawthorn extract, Juniper extract, Jujube extract, Dukes extract, tomato extract, grape extract, sponge gourd extract, lime juice, apple extract, apple juice, lemon extract and lemon juice), medicinal herb extract, vitamin E, vitamin D and the like vitamins as well as kojic acid, arbutin, derivatives thereof and hormones showing skin-whitening action. Not a few of these medicines (effective ingredients) to be contained in the cosmetic pack sheet are liable to be influenced by ultraviolet light. Further, the sheet is applied to a part of a face directly receiving the ultraviolet light. It is, therefore, very desirable that the backing of the sheet be give an ultraviolet-screening property.

The bases to be used for the present patch are not particularly limited as long as they are adhesive to the skin at ordinary temperatures and illustratively include conventional bases containing a water-soluble polymer used for gel patches and cosmetic pack sheets, conventional acrylic bases, rubber-based bases and silicone-based bases used for tape-aids, etc.

The water-soluble polymer illustratively includes thickeners (e.g. synthetic water-soluble polymers such as sodium polyacrylate, polyacrylic acid, poval, polyvinylpyrrolidone, polyethylene oxide, polyvinyl methacrylate, methyl vinyl ether/maleic anhydride copolymer, N-vinylacetamide and N-vinylacetamide copolymers, natural products such as arabic gum, starch and gelatin as well as methyl cellulose, hydroxypropyl cellulose, alginic acid, sodium alginate, ammonium alginate and sodium carboxymethyl cellulose). The content of these thickeners is preferably 6–25% by mass, more preferably 9–16% by mass based on the total amount of the base. Of these thickeners, the polyacrylic acid and its salts showing a high gelling strength and an excellent water retention are particularly preferable, and sodium polyacrylate with 20,000–70,000 of average polymerization degree is more preferable. As the average polymerization degree becomes less than 20,000, the thickener will show less thickening effects with an inclination not to exhibit a sufficient gelling strength. On the other hand, as the average polymerization degree becomes more than 70,000, the thickening effect will become too strong with an inclination to lower workability.

The base containing the water-soluble polymer mentioned above as main ingredient may further contain one or more ingredients selected from, on the basis of the total amount of the base, preferably 5–30% by mass, more preferably 8–25% by mass of wetting agents (e.g. urea, glycerin, propylene glycol, polyethylene glycol, butylene glycol, sorbitol), preferably not more than 15% by mass, more preferably not more than 10% by mass of fillers (e.g. kaolin, zinc oxide, talc, titanium oxide, synthetic aluminum silicate, bentonite), preferably 0.005–15% by mass, more preferably 0.005–10% by mass of cross-linking agents (e.g. polyvalent metal compounds such as aluminum hydroxide, calcium hydroxide, calcium chloride, aluminum sulfate, aluminum ammonium sulfate, aluminum potassium sulfate, magnesium aluminate metasilicate and dihydroaluminum aminoacetate, and epoxy compounds such as ethylene glycol diglycidyl ether, polyethylene glycol diglycidyl ether, propylene glycol diglycidyl ether, polypropylene glycol diglycidyl ether, polytetramethylene glycol diglycidyl ether, glycerol polyglycidyl ether, sorbitol polyglycidyl ether, sorbitan polygycidyl ether, trimethylol-propane polyglycidyl ether, pentaerythritol polyglycidyl ether, resorcin diglycidyl ether, neopentylglycol diglycidyl ether and 1,6-hexanediol diglycidyl ether), preferably 10–90% by mass, more preferably 30–87% by mass of water, and additionally organic acids (e.g. citric acid, tartaric acid, maleic acid, maleic anhydride, succinic acid), solubilization acids for medicines and absorption accelerators for medicines.

The water-soluble polymer base (plaster) suitably containing appropriate amounts of the above ingredients desirably has such a pH value in consideration as not to irritate the skin and desirably has a pH of 4–8, preferably a pH of 5.0–7.5.

An appropriate main polymer ingredient of the acrylic base is especially a copolymer of alkyl (meth)acrylate obtainable from an aliphatic alcohol of 4–18 carbon atoms and (meth)acrylic acid with vinylpyrrolidone or other functional monomers. The content of this copolymer on the basis of the total amount of the base is preferably 60–99% by mass, more preferably 75–98% by mass.

The alkyl (meth)acrylate as above illustratively includes n-butyl (meth)acrylate, isobutyl (meth)acrylate, hexyl acrylate, octyl (meth)acrylate, isooctyl (meth)acrylate, decyl (meth)acrylate, isodecyl (meth)acrylate, lauryl (meth) acrylate, stearyl (meth)acrylate and 2-ethylhexyl acrylate.

The functional monomers include those monomers containing a hydroxyl group, carboxyl group, amino group or amido group.

The monomers having a hydroxyl group illustratively include hydroxyalkyl (meth)acrylates such as 2-hydroxyethyl (meth)-acrylate and hydroxypropyl (meth) acrylate.

The monomers having a carboxyl group illustratively include α,β-unsaturated carboxylic acids such as (meth) acrylic acid; monoalkyl maleate such as butyl maleate; maleic acid (anhydride), fumaric acid and crotonic acid.

The monomer having an amino group illustratively includes dimethylaminoethyl acrylate.

The monomers having an amido group illustratively include (meth)acrylamide such as acrylamide, dimethylacrylamide and dimethylacrylamide; alkyl ether methylol (meth)acrylamide such as butoxymethylacrylamide and ethoxymethylacrylamide; and diacetoneacrylamide.

Other functional monomers than those mentioned above are also available and include vinyl acetate, vinyl alcohol, styrene, α-methylstyrene, vinyl chloride, acrylonitrile, ethylene, propylene and butadiene.

Main polymer ingredients of the rubber-based base include synthetic or natural rubbers such as polyisoprene rubber, polyisobutylene rubber, natural rubber, styrene-butadiene-styrene block copolymer, styrene-isoprene-styrene block copolymer, styrene-butadiene copolymer, styrene-isoprene copolymer, styrene-isoprene-butadiene block copolymer and styrene-ethylene-propylene-styrene block copolymer.

In particular, the rubber-based base may contain additionally oils and fats or higher fatty acids, and tackifiers.

The oils and fats or the higher fatty acids illustratively include almond oil, olive oil, camellia oil, peanut oil, olein oil, liquid paraffin, liquid polybutene, liquid isobutylene and mineral oil.

The tackifiers illustratively include rosins, rosin-denatured maleic acid resins, hydrogenated rosin ester resins, polyterpene resins, cumarone-indene resin, petroleum resins and terpene phenol resins.

Main polymer ingredients for the silicone-based base include silicone rubbers such as polyorganosiloxane.

Further, the base of the patch of the present invention may contain, as conventional additive ingredients, fillers (e.g. zinc oxide, aluminum oxide, titanium dioxide, calcium carbonate, synthetic aluminum silicate, silica, magnesium oxide, stearic acid metal salts), anti-oxidants (e.g. ascorbic acid, tocopherol acetate, natural vitamin E, dibutylhydroxytoluene, propyl gallate), solubilizers or absorption accelerators for medicines or aromatics (e.g. oleic acid, glycol salicylate, benzyl alcohol, isopropyl myristate, crotamiton, oleyl alcohol, peppermint oil, eucalyptus oil, limonene, isopulegol, and other essential oils). Furthermore, surfactants, flavouring agents and the like may be added according to necessity. In addition, counterirritants such as L-menthol, camphor, peppermint oil, red pepper extract, capsaicine, benzyl nicotinate, methyl salicylate and glycol salicylate may be added appropriately if necessary.

The surface of the base for the patch of the present invention may be covered with a releasable cover which is appropriately selected from films provided with releasability such as release paper, cellophane, polyethylene, polypropylene and polyester. These releasable covers protect the base and will be peeled from the base at the time of applying the patch to the skin.

Further, a formula for a tape-aid containing a non-steroidal anti-inflammatory analgesic, which is a particularly useful medicine in the present invention, will be more detailed. In this formula, it is most preferable to use ketoprofen in an amount of 0.1–7.0% by mass based on the total amount of the base. The styrene-isoprene-styrene block copolymer which in an adhesive ingredient of the base preferably has a weight average molecular weight of 100,000–300,000 and illustratively includes Krayton D-KX401CS or D-1107CU (Shell Chemical Co., Ltd.), SIS-5000 or SIS-5002 (Japan Synthetic Rubber Co., Ltd.), QUINTAC 3530, 3421 or 3570C (Nippon Zeon Co., Ltd.) or Solprene 428 (Phillips Petroleum Co., Ltd.). The base may contain one or more of these styrene-isoprene-styrene block copolymers, and content of the copolymers is preferably 10–50% by mass, more preferably 13–40% by mass, still more preferably 15–30% by mass based on the total amount of the base.

The base of the tape-aid of the present invention will highly improve in adhesion to the skin, pain in peeling, skin eruptions and so on by containing the styrene-isoprene-styrene block copolymer having the weight average molecular weight mentioned above and in the amount mentioned above and more preferably further by being adjusted in viscosity and adhesive strength. If the base contains less than 10% by mass of the copolymer, the base will lower unfavorably in cohesive strength and shape retention. A base containing it more than 50% by mass will undesirably have such a high cohesion as to decrease in adhesive strength, evenness of the plaster, and workability.

Further, the base for the tape-aid of the present invention may contain a polyisobutylene, and its content based on the total amount of the base is preferably 1–20% by mass, more preferably 2–18% by mass. Two or more kinds of polyisobutylenes having different average molecular weights may be used in combination. For example, a combination of polyisobutylene having a viscosity-average molecular weight (Staudinger method) of 5,000–15,000 and another polyisobutylene having a viscosity-average molecular weight of 50,000–200,000 is preferred. It is more preferable to use these polyisobutylenes in a specific ratio.

The polyisobutylene having a viscosity-average molecular weight of 5,000–15,000 illustratively includes Vistanex LM-MS and LM-MH (EXXON CHEMICAL JAPAN LTD.), Tetrax 4T, 5T and 6T (Nippon Petrochemicals Co., Ltd.) and Opanol B12SF and B15SF (BASF Japan Co., Ltd.), and one or more of which may be contained in the base for a tape-aid. The content of the polyisobutylene based on the total amount of the base is preferably 1–20% by mass, more preferably 2–18% by mass, still more preferably 4–15% by mass. A base containing it in an amount of less than 1% by mass will lack the adhesive strength. A base containing it more than 20% by mass will unfavorably lower in cohesive strength, shape retention and so on.

The polyisobutylene having a viscosity-average molecular weight of 50,000–200,000 illustratively includes Vistanex MML-80, MML-100, MML-120 and MML-140 (EXXON CHEMICAL JAPAN LTD.) and Opanol B80, B100, B120 and B150 (BASF Japan Co., Ltd.), and one or more thereof may be contained in the base of a tape-aid. The content thereof based on the total amount of the base is preferably 0.1–20% by mass, more preferably 1–18% by mass and still more preferably 3.6–10% by mass. By adopting these mixing ratios, more preferably further by regulating the viscosity and adhesive strength, the base will highly improve in adhesive strength, adhesion to the skin for a long time, pain at the time of peeling, skin eruptions and so on. A base containing less than 0.1% by mass of the polyisobutylene having a viscosity-average molecular weight of 50,000–200,000 will unfavorably lower in strength and shape retention. A base containing it more than 20% by mass will undesirably have such a high cohesion as to decrease in adhesive strength, evenness of the plaster, and workability.

When two or more kinds of polyisobutylene having different viscosity-average molecular weights are used, it is preferable that the whole amount of the polyisobutylenes not exceed 20% by mass based on the total amount of the base.

The adhesive base to be used for the patch of the present invention has a viscosity of preferably 1,500–30,000 poise @60° C., more preferably 2,000–20,000 poise @60° C. and an adhesive strength of preferably 5–200 g/10 mm, more preferably 20–150 g/10 mm. Further, a preferable patch of the present invention has an adhesive base which has a ratio of viscosity value (poise @60° C.) divided by adhesive strength (g/10 mm) (viscosity value/adhesive strength) of preferably 10–400, more preferably 30–200. Accordingly, a patch of a preferred embodiment of the present invention has an adhesive base composed of a styrene-isoprene-styrene block copolymer, a polyisobutylene, a tackifier, a plasticizer and a medicinal ingredient, said base having a viscosity of 1,500–30,000 poise @60° C. and an adhesive strength of 5–200 g/10 mm with the viscosity value (poise @60° C.) being 10–400 times as large as the adhesive strength (g/10 mm). The patch showing such physical values can maintain adhesion to the skin for a long time and lower the pain at the time of peeling, skin eruptions and damage to the keratin layer. In this connection, a patch deviating from these physical values will be unfavorable in regard to adhesion to bending parts, pain at the time of peeling, damage to the keratin layer, skin eruptions, stickiness, and so on.

A preferred adhesive base according to the present invention containing a styrene-isoprene-styrene block copolymer, a polyisobutylene, a tackifier and a plasticizer can be prepared by mixing the styrene-isoprene-styrene block copolymer, the polyisobutylene and the tackifier in a desired ratio and regulating the resulting mixture with the plasticizer so as to have the viscosity mentioned above. The adhesive strength of the patch of the present invention can be regulating by adjusting mainly the composition of the adhesive base.

Prefered tackifiers have a softening point of 60–150° C. and illustratively include rosin esters, hydrogenated rosin esters, maleic acid-denatured rosin esters, polyterpene resins and petroleum resins, such as Ester Gum A, AA–G, H or HP (Arakawa Chemical Industry Co., Ltd.), Hariester L, S or P (Harima Chemicals Co., Ltd.), Pine Crystal KE-100 or KE-311 (Arakawa Chemical Industry Co., Ltd.), Hercolyn D (RIKA HERCULES INC.), Foral 85 or 105 (RIKA HERCULES INC.), Stebelite Ester 7 or 10 (RIKA HERCULES INC.), Pentalyn 4820 or 4740 (RIKA HERCULES INC.), Arkon P-85 or P-100 (Arakawa Chemical Industry Co., Ltd.), Escorez 5300 (EXXON CHEMICAL JAPAN LTD.), Clearon K, M or P (Yasuhara Chemical Co., Ltd.). One or more of them may be contained in the adhesive base. The content of the tackifier on the total amount of the base is preferably 5–50% by mass, more preferably 7–45% by mass, still more preferably 10–40% by mass, and it may be used to regulate the viscosity and adhesive strength of the base within the above-mentioned range. Those ratios will highly improve the resultant base in adhesive strength, adhesion to the skin, pain at the time of peeling, skin eruptions and so on. A base containing less than 5% by mass of the tackifier is not preferable because such a base will decrease in adhesive strength and adhesion to the skin. A base containing it more than 50% by mass is not preferable because it will lower in shape retention and increase in pain at the time of peeling, damage to the keratin layer, skin eruptions, stickiness and so on.

The plasticizer favorably has a solution viscosity of 10–100 cSt @40° C. and illustratively includes almond oil, olive oil, camellia oil, persic oil, peanut oil, olefinic acid and liquid paraffin. One or more of them may be contained in the adhesive base. The mixing ratio is preferably 10–70% by mass, more preferably 15–60% by mass, still more preferably 20–55% by mass, based on the total amount of the base and it may be added so as to adjust the viscosity and adhesive strength of the base within the above-mentioned range. Adoption of those mixing ratios will highly improve the resulting base in adhesive strength, adhesion to the skin, homogeneous dispersibility of a medicine in the base, pain at the time of peeling, damage to the keratin layer, skin eruptions, thermostability and so on. If the content of the plasticizer is less than 10% by mass, it will unfavorably lower the base in adhesive strength, adhesion to the skin and dispersibility of the medicine and also lower the evenness of the base (plaster) and workability due to elevation of the viscosity of the plaster. If the content exceeds 70% by mass, it will unfavorably lower percutaneous absorption of the medicine and shape retention of the base and raise pain at the time of peeling, damage to the keratin layer, skin eruptions, stickiness and so on.

Further, the material to be used as a backing in the present invention is selected from films, cloth and non-woven cloth of polyethylene, polypropylene, polybutadiene, polyester, nylon, polyurethane, etc.

Of these materials, the polyester cloth is preferably used, because it has a good feel and usage sense. Further, these backings preferably have a mass of 70–130 g/cm² and a thickness of 0.1–2 mm. If the mass per unit area or thickness of the backing is below the lower limit, the patch (laminate of the backing and a base) will be liable to wrinkle or get entangled without affording good usage sense. If it exceeds the upper limit, the patch (laminate) will lack flexibility so that there is an inclination to bring about a sense of incongruity such as drawing feel at the time of sticking.

A backing being stretchable is most suitable, and the stretchable backing to be used in the present invention preferably bears a load at the time of 50% elongation of 0.98–14.71 N/5 cm in each of the long-side and short-side directions, more preferably 1.96–9.81 N/5 cm in the long-side direction and 0.98–9.81 N/5 cm in the short-side direction. If the backing bears a load at 50% elongation of below the lower limit, it will be too weak-kneed to hold the base firm with an inclination hard to get good usage sense at the time of sticking. If the backing bears a load at 50% elongation exceeding said upper limit, the patch will insufficiently follow the move of the skin and tend to easily peel off even by a small move of a joint part such as an elbow or knee in the case of sticking the patch thereto. The load at the time of 50% elongation used herein refers to the value measured according to the method in the item "Load for Stretching" in JIS General Fabric Test Method L1096 provided that the 80% of the elongation at the time of loading 1.5 kgf is replaced by 50% of the distance between the gripping portions. Thus, the load at the time of 50% elongation according to the present invention refers to the force per unit width [5N/cm] when a test piece of 30 cm long and 5 cm wide is pulled in each of the long side and short side directions at tensile rate of 200 mm/min with a distance between the gripping portions of 20 cm by the use of a tensile test machine as defined in JIS Z 0237 and has reached 50% elongation along the test side on the basis of the distance between the gripping portions (it means that the distance between the gripping portions along the test side has become 30 cm).

Further, the stretchable backing to be used in the present invention shows a recovering rate at the time of 50% elongation of preferably 50–95% in each of the long side and short side directions, more preferably 50–95% in the long side direction and 60–90% in the short side direction If the recovering rate at 50% elongation of the backing is below the lower limit, the resultant patch will insufficiently follow the move of the skin and tend to easily peel off even by a small move in the case of sticking the patch to the joint part such as an elbow or knee. On the other hand, the follow-up to the skin will increase together with elevation of the recovering rate at 50% elongation of the backing but, if the rate exceeds said upper limit, the patch (laminate) applied tends to wrinkle and get interlocked to hardly give good usage sense. The recovering rate at 50% elongation herein refers to the value measured according to Method A (Repeated constant elongation at constant speed method) of "Elongation Recovering Rate and Residual Strain Rate" in JIS General Fabric Test Method L1096 provided that the 80% of the elongation at the time of loading 1.5 kgf is replaced by 50% of the distance between the grip sections. Thus, the recovering rate at 50% elongation according to the present invention refers to the value [%] obtained by 1) pulling a test piece of 30 cm long and 5 cm wide in each of the long side and short side directions at tensile rate of 200 mm/min with a distance between the gripping portions of 20 cm by the use of a tensile test machine as defined in JIS Z 0237 until the piece reaches 50% elongation along the test side based on the distance between the gripping portions (it means that the distance between the gripping portions along the test sides has become 30 cm), followed by allowing it to leave for 1 minute, 2) putting the test piece back to the original position at a rate of 200 mm/min and allowing it to leave for 3 minutes, 3) repeating both the steps 5 times, 4) subtracting the length to the first loading point (residual strain) from the length of the gripping portions when further pulling the piece at a rate of 200 mm/min, and dividing the difference with said length of the gripping portions.

Then, a process for manufacturing the patch of the present invention will be explained below by giving one example. To a mixture of styrene-isoprene-styrene block copolymer and polyisobutylene are added a tackifier and a plasticizer for regulating the viscosity and adhesive strength. A filler and an anti-oxidant are optionally added in prescribed ratios to give a mixture, which is then heated with stirring in a nitrogen atmosphere to give a solubilized material Temperature at the stirring is 110–200° C., and stirring period is 30–120 minutes. Then, a medicinal ingredient is added at 110–200° C. during stirring the solubilized material, and the mixture is stirred for 1–30 minutes to give a homogeneous solubilized material. Subsequently, the solubilized material is spread in a conventional manner directly on the backing pretreated with the special processing with an ultraviolet absorbent and/or ultraviolet-screening agent and then covered with a release cover, or the material may alternatively be once spread on a release cover and then covered with a backing and pressure-contact transferred. The release cover may be appropriately selected from a release paper pretreated for releasing, cellophane, and films of polyethylene, polypropylene, polyester, etc.

The mixing order of the raw materials, medicinal ingredients and other ingredients in the above process is illustrated as one example, and the present invention will not be limited to this mixing order.

The patch of the present invention has the following excellent features because its backing has been processed for screening the ultraviolet.

1) Sufficient therapeutic effect can be expected, because the patch is high in photostability of the medicine and does not lower the content.
2) Photolysis of the medicine is lowered so much that there may be produced neither allergy due to photolyzed products nor toxicity.
3) There is no need of adding an ultraviolet absorbent or the like into the base in order to increase the photostability of the medicine.
4) Because the backing is a single layer, the patch is so excellent in adhesion to the skin that absorption of the medicine as an effective ingredient may be promoted.
5) Manufacturing cost can be reduced because of using a single-layered backing.
6) Because an organic ultraviolet absorbent is adsorbed onto the single-layered backing or an inorganic ultraviolet-screening agent is kneaded into it, the ingredients of the adhesive base will not ooze or deeply permeate into the backing. As a result, the adhesive strength of the surface of the backing increases to give an optimal form of patch.

BEST MODE FOR CARRYING OUT THE INVENTION

Figure 1:
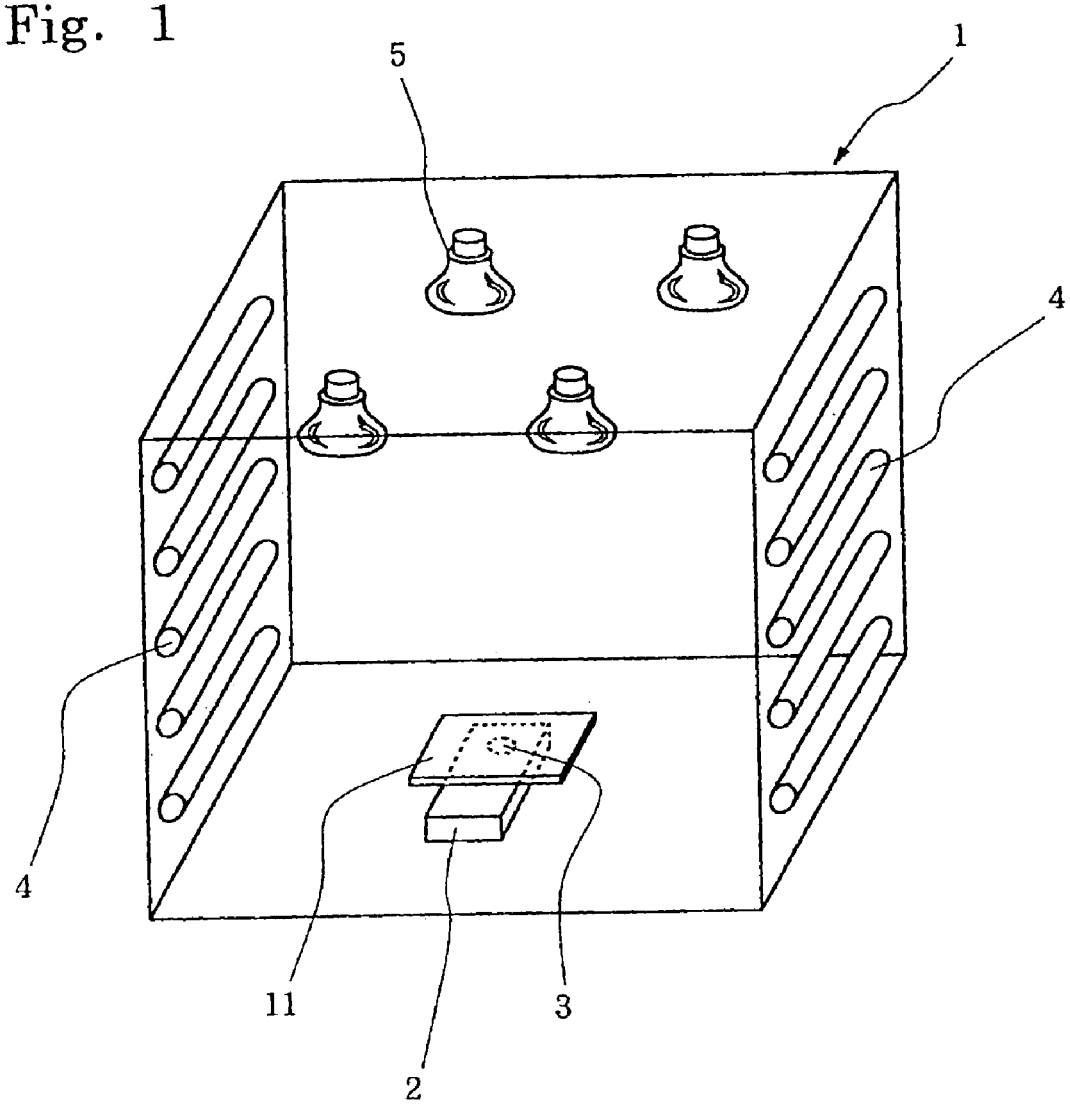
FIG. 1 is a perspective view of an artificial meteorological apparatus used in photo-transmission test.

Formulations of the base for the patch of the present invention will be illustrated in greater detail, but the Examples should not be construed as limiting the scope of the invention.

Formulation 1

Into a mixer were introduced 52 parts by mass of purified water, 3 parts by mass of gelatin, 2 parts by mass of polyvinyl alcohol (Gohsenol GH-20: manufactured by The Nippon Synthetic Chemical Industry Co., Ltd.) and 3 parts by mass of kaolin, and the mixture was dissolved at about 50° C. to give a uniform dispersion. To this dispersion was added a previously prepared dispersion of 30 parts by mass of glycerin, 3 parts by mass of sodium polyacrylate (Viscomate NP-700: manufactured by Showa Denko K. K.), 3 parts by mass of methyl vinyl ether-maleic anhydride copolymer (Gantrez AN-119: manufactured by ISP) and 2 parts by mass of aluminum hydroxide, and the whole was stirred. Then, a solution of 0.5 parts by mass of ketoprofen in 1.5 parts by mass of peppermint oil was added and stirred to give a homogeneous mixture as a base for a gel patch.

Formulation 2

Into a mixer were introduced 33.92 parts by mass of purified water, 3 parts by mass of gelatin, 2 parts by mass of polyvinylpyrrolidone (kollidon K30: manufactured by BASF) and 3 parts by mass of zinc oxide, and the mixture was dissolved at about 50° C. to give a homogeneous dispersion. To this dispersion was added a previously prepared dispersion of 50 parts by mass of polyethylene glycol (Macrogol 400: manufactured by NOF CORPORATION), 3 parts by mass of sodium polyacrylate (Viscomate H-480: manufactured by Showa Denko K.K.), 3 parts by mass of polyacrylic acid (Junlon PW-111: manufactured by Nihonjunyaku Co., Ltd.) and 0.08 parts by mass of polyethylene glycol glycidyl ether, and the resultant mixture was stirred. Then, a previously prepared solution of 0.5 parts by mass of suprofen in 1.5 parts by mass of benzyl alcohol was added and stirred to give a homogeneous mixture as a base for a gel patch.

Formulation 3

Into a mixer were added 47.47 parts by mass of purified water, 1 part by mass of agar-agar, 2 parts by mass of polyvinyl alcohol (Gorsenol GH-20: manufactured by The Nippon Synthetic Chemical Industry Co., Ltd.) and 2 parts by mass of titanium oxide, and the mixture was dissolved at about 50° C. to give a homogeneous dispersion. To this dispersion was added a previously prepared dispersion of 26 parts by mass of glycerin, 15 parts by mass of sorbitol, 3.2 parts by mass of sodium polyacrylate (Viscomate H480: manufactured by Showa Denko K. K.), 2.5 parts by mass of polyacrylic acid (Junlon PW-111: manufactured by Nihonjunyaku Co., Ltd.) and 0.03 parts by mass of polyglycerol polyglycidyl ether, and the whole was stirred. Then, a previously prepared solution of 0.5 parts by mass of pyroxicam in 0.3 parts by mass of crotamiton was added and stirred to give a homogeneous mixture as a base for a gel patch.

Formulation 4

A mixture of 22 parts by mass of styrene-isoprene-styrene block copolymer (Krayton D-1107CU: manufactured by Shell Chemcal), 22 parts by mass of polyisobutylene (Opanol B80: manufactured by BASF), 12 parts by mass of hydrogenated rosin ester (Stebelight Ester: manufactured by RIKA HERCULES INC.), 40 parts by mass of liquid paraffin (Crystol J-352: manufactured by Esso Sekiyu K. K.) and 1 part by mass of dibutylhydroxytoluene was stirred in a temperature range of 110–200° C. for 30–120 minutes in a nitrogen atmosphere to give solubilized material. Then, 3 parts by mass of ketoprofen was added to the solution within a temperature range of 110–200° C. with stirring, which was stirred for another 5–30 minutes to give a homogeneous solubilized material as a base for a tape-aid.

Formulation 5

A mixture of 15 parts by mass of styrene-isoprene-styrene block copolymer (Krayton D-1107CU: manufactured by Shell Chemical Co., Ltd.), 26 parts by mass of polyisobutylene (Tetrax 6T: manufactured by Nippon Petrochemicals), 13 parts by mass of maleic acid hydrogenated rosin ester (Malkyd: manufactured by Arakawa Chemical Industry Co., Ltd.) and 41 parts by mass of liquid paraffin (Crystol J-352) was stirred at 110–200° C. in a nitrogen atmosphere for 30–120 min to give a solubilized material. Then, to this solubilized material were added 3 parts by mass of naproxen and 2 parts by mass of L-menthol at 110–200° C. with stirring, and the mixture was stirred for another 5–30 min to give a homogeneous solubilized material as a base for a tape-aid.

Formulation 6

A mixture of 23 parts by mass of styrene-isoprene-styrene block copolymer (Clayon D-KX401CS: manufactured by Shell Chemical Co., Ltd.), 22 parts by mass of polyisobutylene (Bistanecs MML-80: EXXON CHEMICAL JAPAN LTD.), 23 parts by mass of petroleum resin (Escorettu 5300: manufactured by EXXON CHEMICAL JAPAN LTD.), 24 parts by mass of liquid paraffin (Crystol J-352: manufactured by Esso Sekiyu K.K.) and 3 parts by mass of titanium oxide was stirred at 110–200° C. in a nitrogen atmosphere for 30–120 mm to give a solubilized material. Then, to this solubilized material was added 5 parts by mass of sodium diclofenac at 110–200° C. with stirring, and the resultant mixture was stirred further for 5–30 min to give a homogenous solubilized material as a base for a tape-aid.

Formulation 7

Into a reactor were added 55 parts by mass of 2-ethylhexyl acrylate, 26 parts by mass of methoxyethyl acrylate, 14.7 parts by mass of vinyl acetate, 0.3 parts by mass of azobisiso-butyronitrile and 100 parts by mass of ethyl acetate. The mixture was heated up to 65° C. in a nitrogen atmosphere to start polymerization. The reaction was carried out for 10 hours and matured further at 80° C. for 2 hours to give a solution of copolymer. To this copolymer solution thus obtained was added 4 parts by mass of ketoprofen, and the mixture was stirred to give a homogenous mixed solution as a base solution for a tape-aid.

Formulation 8

A mixture of 25 parts by mass of styrene-isoprene-styrene block copolymer (Krayton D-KX401CS: manufactured by Shell Chemical Co., Ltd.), 10 parts by mass of polyisobutylene (Vistanex MML-100: manufactured by EXXON CHEMICAL JAPAN LTD.), 25 parts by mass of hydrogenated rosin glycerin ester (manufactured by Arakawa Chemical), 35 parts by mass of liquid paraffin (Crystol J-352: manufactured by Esso Sekiyu K.K.) and 3 parts by mass of synthetic aluminum silicate was stirred at 110–200° C. in a nitrogen atmosphere for 30–120 min to give a solubilized material. Then, to this solubilized material was added 2 parts by mass of morphine hydrochloride at 110–200° C. with stirring, and the mixture was stirred for another 5–30 min to give a homogenous solubilized material as a base for a tape-aid.

Formulation 9

To a reactor were added 55 parts by mass of 2-ethylhexyl acrylate, 25 parts by mass of methoxyethyl acrylate, 15 parts by mass of vinylpyrrolidone, 1.0 part by mass of benzoyl peroxide and 100 parts by mass of ethyl acetate, and the resultant mixture was heated up to 65° C. in a nitrogen atmosphere to start polymerization. The reaction was carried out for 10 hours and matured further at 80° C. for 2 hours to give a copolymer solution. To the copolymer solution thus obtained was added 4 parts by mass of ketotifen fumarate, and the mixture was stirred to give a homogenous mixed solution as a solution base for a tape-aid.

Formulation 10

To a dispersion of 4 parts by mass of synthetic aluminum silicate in 78.4 parts by mass of purified water were added 1 part by mass of gelatin, 0.05 parts by mass of sorbitol polyglycidyl ether, 0.2 parts by mass of water-soluble placenta extract, 0.1 part by mass of allantoin and 0.25 parts by mass of methyl paraben, and the resultant solution was mixed with 6 parts by mass of sodium polyacrylate and 10 parts by mass of polyethylene glycol and stirred until the whole became homogeneous. Thus, a base for a pack sheet was obtained.

Formulation 11

To a dispersion of 5 parts by mass of kaolin and 1 part by mass of aluminum acetate in 71.19 parts by mass of purified water were added 0.5 parts by mass of gelatin, 0.045 parts by mass of grapefruit extract, 0.045 parts by mass of apple extract, 0.003 parts by mass of orange juice, 0.002 parts by mass of lemon juice, 0.005 parts by mass of lime juice and 0.1 part by mass of methyl paraben, and the mixture was stirred to give a solution. To the solution was added a mixture of 7 parts by mass of sodium polyacrylate, 5 parts by mass of polyethylene glycol, 10 parts by mass of polypropylene glycol, 0.1 part by mass of ethyl paraben and 0.01 part by mass of propyl paraben, and the resultant mixture was stirred until the whole became homogeneous. Thus, a base for a pack sheet was obtained.

Examples of the patch of the present invention and Comparative examples will be shown below.

EXAMPLE 1

The base obtained in Formulation 1 was spread on a polypropylene film at a ratio of 10 g/140 cm$^2$. On the other hand, 0.5 parts by mass of 2-(2'-hydroxy-5'-methylphenyl)-benzotriazole was adsorbed onto 99.5 parts by mass of polyester non-woven cloth to give a backing processed for screening ultraviolet light. The above base spread on the film was covered with this backing, pressure-contact transferred and cut into gel patches each of a desired size.

EXAMPLE 2

The base obtained in Formulation 1 was spread on a polyethylene film at a ratio of 10 g/140 cm$^2$. On the other hand, 1 part by mass of 2-hydroxy-4-methoxybenzophenone was adsorbed onto 99 parts by mass of a polypropylene non-woven cloth to give a backing processed for screening ultraviolet light. The above base spread on the film was covered with this backing, pressure-contact transferred and cut into gel patches each of a desired size.

EXAMPLE 3

The base obtained in Formulation 2 was spread on a polyester film at a ratio of 10 g/140 cm$^2$. On the other hand, 6 parts by mass of titanium oxide were kneaded into 94 parts by mass of polyester resin to give a polyester non-woven cloth backing processed for screening ultraviolet light. The above base spread on the film was covered with this backing, pressure-contact transferred and cut into gel patches each of a desired size.

EXAMPLE 4

The base obtained in Formulation 3 was spread on a polyethylene film at a ratio of 10 g/140 cm$^2$. On the other hand, 0.1 part by mass of p-tert-butylphenyl salicylate was adsorbed onto 99.9 parts by mass of a polyester non-woven cloth to give a backing processed for screening ultraviolet light. The above base spread on the film was covered with this backing, pressure-contact transferred and cut into gel patches each of a desired size.

EXAMPLE 5

The base obtained in Formulation 3 was spread on a polypropylene film at a ratio of 10 g/140 cm$^2$. On the other hand, 3 parts by mass of zinc oxide was kneaded into 97 parts by mass of polyester resin to give a polyester non-woven cloth backing processed for screening ultraviolet light. The above base spread on the film was covered with this backing, pressure-contact transferred and cut into gel patches each of a desired size.

EXAMPLE 6

The base obtained in Formulation 4 was spread on a polyester film treated with silicone at a ratio of 1 g/70 cm$^2$. On the other hand, 2 parts by mass of 2-(2'-hydroxy-5'-methylphenyl) benzotriazole was adsorbed onto 98 parts by mass of a polyester woven cloth to give a backing processed for screening ultraviolet light. The above base spread on the film was covered with this backing, pressure-contact transferred and cut into tape-aids each of a desired size.

EXAMPLE 7

The base obtained in Formulation 5 was spread on a polyester film treated with silicone at a ratio of 1 g/70 cm$^2$. On the other hand, 3 parts by mass of 2-hydroxy-4-methoxybenzophenone was adsorbed onto 97 parts by mass of a polyester woven cloth to give a backing processed for screening ultraviolet light. The above base spread on the film was covered with this backing, pressure-contact transferred and cut into tape-aids each of a desired size.

EXAMPLE 8

The base obtained in Formulation 5 was spread on a polyester film treated with silicone at a ratio of 1 g/70 cm$^2$. On the other hand, 3 parts by mass of titanium oxide was kneaded into 97 parts by mass of polyester resin to give a polyester woven cloth backing processed for screening ultraviolet light. The above base spread on the film was covered with this backing, pressure-contact transferred and cut into tape-aids each of a desired size.

EXAMPLE 9

The base obtained in Formulation 6 was spread on a release paper treated with silicone at a ratio of 1 g/70 cm 2.

On the other hand, 3 parts by mass of p-tert-butylphenyl salicylate was adsorbed onto 97 parts by mass of a polyester non-woven cloth to give a backing processed for screening ultraviolet light. The above base spread on the release paper was covered with this backing, pressure-contact transferred and cut into tape-aids each of a desired size.

EXAMPLE 10

The base obtained in Formulation 6 was spread on a polyester film treated with silicone at a ratio of 1 g/70 cm$^2$. On the other hand, 2 parts by mass of zinc oxide was kneaded into 98 parts by mass of polyester resin to give a polyester woven cloth backing processed for screening ultraviolet light. The above base spread on the film was covered with this backing, pressure-contact transferred and cut into tape-aids each of a desired size.

EXAMPLE 11

The base solution obtained in Formulation 7 was spread on a polyester film treated with silicone to be at a ratio of 0.5 g/70 cm$^2$ after dried. On the other hand, 1 part by mass of 2-(2'-hydroxy-5'-methylphenyl) benzotriazole was adsorbed onto 99 parts by mass of a polyester woven cloth to give a backing processed for screening ultraviolet light. The above base spread on the film was covered with this backing, pressure-contact transferred and cut into tape-aids each of a desired size.

EXAMPLE 12

The base solution obtained in Formulation 7 was spread on a polyester film treated with silicone to be at a ratio of 0.5 g/70 cm$^2$ after dried. On the other hand, 0.1 part by mass of 2-hydroxy-4-methoxybenzophenone was homogeneously added into 99.9 parts by mass of a polyvinyl chloride film to give a backing processed for screening ultraviolet light. The above base spread on the film was covered with this backing, pressure-contact transferred and cut into tape-aids each of a desired size.

EXAMPLE 13

The base solution obtained in Formulation 7 was spread on a polyester film treated with silicone to be at a ratio of 0.5 g/70 cm$^2$ after dried. On the other hand, 0.5 parts by mass of titanium oxide was kneaded into 99.5 parts by mass of polyester resin to give a polyester woven cloth backing processed for screening ultraviolet light. The above base spread on the film was covered with this backing, pressure-contact transferred and cut into tape-aids each of a desired size.

EXAMPLE 14

The base obtained in Formulation 8 was spread on a polyester film treated with silicone at a ratio of 1 g/70 cm$^2$. On the other hand, 5 parts by mass of titanium oxide was kneaded into 95 parts by mass of polyester resin to give a polyester woven cloth backing processed for screening ultraviolet light. The above base spread on the film was covered with this backing, pressure-contact transferred and cut into tape-aids each of a desired size.

EXAMPLE 15

The base solution obtained in Formulation 9 was spread on a polyester film treated with silicone to be at a ratio of 0.5 g/70 cm$^2$ after dried. On the other hand, 0.1 part by mass of 2-hydroxy-4-methoxybenzophenone was homogeneously added to 99.9 parts by mass of a polyethylene vinyl acetate (EVA) film to give a backing processed for screening ultraviolet light. The above base spread on the film was covered with this backing, pressure-contact transferred and cut into tape-aids each of a desired size.

EXAMPLE 16

The base obtained in Formulation 10 was spread on a polypropylene film at a ratio of 14 g/140 cm$^2$. On the other hand, 0.3 parts by mass of 2-(2'-hydroxy-5'-methylphenyl) benzotriazole was adsorbed onto 99.7 parts by mass of a polyester non-woven cloth to give a backing processed for screening ultraviolet light. The above base spread on the film was covered with this backing pressure-contact transferred and cut into pack sheets each of a desired size.

EXAMPLE 17

The base obtained in Formulation 11 was spread on a polyester film at a ratio of 14 g/140 cm$^2$. On the other hand, 7 parts by mass of titanium oxide was kneaded into 93 parts by mass of polyester resin to give a polyester woven backing processed for screening ultraviolet light. The above base spread on the film was covered with this backing, pressure-contact transferred and cut into pack sheets each of a desired size.

EXAMPLE 18

The base obtained in Formulation 4 was spread on a polyester film treated with silicone at a ratio of 1 g/70 cm$^2$. On the other hand, 2.5 parts by mass of 2-(2'-hydroxy-5'-methylphenyl) benzotriazole was allowed to adsorb onto a woven cloth of 96 parts by mass of polyester resin kneaded with 1.5 parts by mass of titanium oxide, to thereby obtain a polyester woven cloth backing processed for screening ultraviolet light. The above base spread on the film was covered with this backing, pressure-contact transferred and cut into tape-aids each of a desired size.

COMPARATIVE EXAMPLE 1

In 25.5 parts by mass of purified water was swollen 2 parts by mass of carboxyvinyl polymer (Hibis Wako 104: manufactured by Wako Pure Chemical Industries, Ltd.). A solution of 3 parts by mass of ketoprofen in 40 parts by mass of ethyl alcohol and 2 parts by mass of diisopropyl adipate was added thereto and stirred. Then, a solution of 2 parts by mass of hydroxypropyl cellulose in 15 parts by mass of propylene glycol was added to the mixture, which was stirred. A solution of 2.5 parts by mass of diisopropanolamine in 8 parts by mass of purified water was added thereto and sufficiently stirred until the whole became homogeneous. Thus, a gel was obtained.

COMPARATIVE EXAMPLE 2

To a solution of 1 part by mass of ketoprofen in 38.5 parts by mass of ethanol were added 12 parts by mass of propylene glycol, 0.8 parts by mass of methyl cellulose and 2 parts by mass of diethyl sebacate, and the resultant mixture was sufficiently stirred and dispersed. To this mixture was added a solution of 0.07 parts by mass of potassium hydroxide in 45.63 parts by mass of purified water with stirring, and the mixture was stirred until the whole became homogeneous. Thus, a liniment was obtained.

COMPARATIVE EXAMPLE 3

The base obtained in Formulation 1 was spread on a polyethylene film at a ratio of 10 g/140 cm$^2$, covered with a backing of polyester non-woven cloth, pressure-contact transferred and cut into gel patches each of a desired size.

COMPARATIVE EXAMPLE 4

The base obtained in Formulation 4 was spread on a polyester film treated with silicone at a ratio of 1 g/70 cm$^2$, covered with a backing of polyester woven cloth, pressure-contact transferred and cut into tape-aids each of a desired size.

COMPARATIVE EXAMPLE 5

The base obtained in Formulation 7 was spread on a polyester film treated with silicone at a ratio of 0.5 g/70 cm$^2$, covered with a backing of polyvinyl chloride film, pressure-contact transferred and cut into tape-aids each of a desired size Phototransmission Test 1

The backings prepared in Examples 1 to 7, 10, 12, 14 and 15 and Comparative Examples 3 to 5 were tested for photo transmission.

More specifically, a measuring part 3 of an ultraviolet intensitometer 2 installed in an artificial meteorological apparatus 1 as shown in FIG. 1 was covered with each of the backings 11 (square of 10 cm×10 cm) used in the Examples and Comparative Examples. The backing 11 over the measuring part 2 was irradiated by fluorescent lamps 4 and sunlight lamps 5 to thereby observe the ultraviolet intensity indicated by the ultraviolet intensitometer 2 and then calculate the phototransmission rate of each backing 11 on the basis of the ultraviolet intensity (as photo transmission rate of 100%) indicated in the condition of not being covered with a backing (Environment in the apparatus: temperature= 25° C., ultraviolet intensity=about 0.14 mW/hr/cm$^2$). As seen from the test results in Table 1, the backings of the Examples of the present invention showed a phototransmission rate of 1.8–25.8%, which were clearly lower than those shown by the backings of the Comparative Examples.

TABLE 1

| Backing | Phototransmission rate (%) |
|---|---|
| Ex. 1 | 2.0 |
| Ex. 2 | 3.6 |
| Ex. 3 | 7.8 |
| Ex. 4 | 8.8 |
| Ex. 5 | 12.3 |
| Ex. 6 | 1.8 |
| Ex. 7 | 5.2 |
| Ex. 10 | 10.3 |
| Ex. 12 | 25.8 |
| Ex. 14 | 8.2 |
| Ex. 15 | 7.7 |
| Comp. Ex. 3 | 62.3 |
| Comp. Ex. 4 | 53.0 |
| Comp. Ex. 5 | 81.3 |

Photostability Test 1

A photostability test was carried out on the medicines in the preparations of Examples 1–13 and Comparative Examples 1–5. More specifically, the gel and liniment of Comparative Examples 1–2 were thinly coated on a glass plate while the patches were placed with the backing side upward. These preparations were allowed to leave at a place that was fully irradiated with the direct sunlight. Eight hours later, the rate of the medicine remaining in each base was measured by liquid chromatography. The results are shown in Table 2.

TABLE 2

|  | Rate of medicinal ingredient remaining (%) |
| --- | --- |
| Ex. 1 | 83 |
| Ex. 2 | 84 |
| Ex. 3 | 81 |
| Ex. 4 | 81 |
| Ex. 5 | 78 |
| Ex. 6 | 83 |
| Ex. 7 | 82 |
| Ex. 8 | 79 |
| Ex. 9 | 77 |
| Ex. 10 | 75 |
| Ex. 11 | 81 |
| Ex. 12 | 74 |
| Ex. 13 | 70 |
| Comp. Ex. 1 | 23 |
| Comp. Ex. 2 | 24 |
| Comp. Ex. 3 | 45 |
| Comp. Ex. 4 | 75 |
| Comp. Ex. 5 | 23 |

As seen from Table 2, all the patches of the present invention showed a high rate of medicine remaining of 70% and more. On the other hand, the preparations of Comparative Examples except for Comparative Example 4 showed a low rate.

Photostability Test 2

A second drug photostability test was carried out on the preparations of Examples 1, 3, 6, 7, 10, 12, 14 and 15, and Comparative Examples 1 and 3–5. More specifically, the gel of Comparative Example 1 was put in a transparent glass vessel, and the patches were placed with the backing sides upward. These were then allowed to leave at a place that was fully irradiated with the direct sunlight. One day, 3 days and 5 days later, the bases were observed for degree of coloration. The results are shown in Table 3.

TABLE 3

|  | 1 day later | 3 days later | 5 days later |
| --- | --- | --- | --- |
| Ex. 1 | No change | Slight yellow | Slight yellow |
| Ex. 3 | No change | No change | Slight yellow |
| Ex. 6 | No change | Slight yellow | Slight yellow |
| Ex. 7 | No change | Slight yellow | Slight yellow |
| Ex. 10 | No change | Slight yellow | Slight yellow |
| Ex. 12 | No change | Slight yellow | Slight yellow |
| Ex. 14 | No change | Slight yellow | Slight yellow |
| Ex. 15 | No change | Slight yellow | Slight yellow |
| Comp. Ex. 1 | Slight yellow | yellow | Brown |
| Comp. Ex. 3 | Slight yellow | yellow | Yellow |
| Comp. Ex. 4 | No change | No change | Slight yellow |
| Comp. Ex. 5 | Slight yellow | yellow | Yellow |

Photostability Test 3

Third drug photostability test was carried out on the patches of Examples 6–8, 10, 12, 16–17, and Comparative Examples 4–5. More specifically, the patches were left, with the backing sides upward, at a place that was fully exposed to the direct sunlight. Eight hours later, the bases were observed for cohesive strength (stickiness). The results are shown in Table 4.

TABLE 4

|  | Stickiness |
| --- | --- |
| Ex. 6 | Non |
| Ex. 7 | Non |

TABLE 4-continued

|  | Stickiness |
| --- | --- |
| Ex. 8 | Non |
| Ex. 10 | Non |
| Ex. 12 | Non |
| Ex. 16 | Non |
| Ex. 17 | Non |
| Comp. Ex. 4 | Present |
| Comp. Ex. 5 | Present |

Table 4 shows that the bases of the patches of the present invention are superior in photostability and usability to those of Comparative Examples 4–5 which were sticky after the irradiation of sunlight for 8 hours.

Skin Photosensitization Test

Skin photosensitization test was carried out on the preparations of Examples 2, 6, 8 and Comparative Examples 1, 4 and 5 according to Adjuvant and Strip method as provided in Guideline for Pharmaceutical Licensing Procedure in Japan (Edited by Japanese Formulation Association, Published by Yakugyou Jihou, 1987).

Photosensitization:

0.1 ml of a water-in-oil (W/O)-type emulsion (E-FCA) of distilled water and Freund's Complete Adjuvant (FCA) (1:1) was intradermally administered at each of 4 corners of previously-shorn neck-back skin (about 2 cm×4 cm) of a guinea-pig. Corneum was peeled off the intradermally injected part with cellophane tape. Each of the preparations of the Examples and Comparative Examples was applied or stuck in an open state to the corneum-peeled part and then irradiated with about 10 Joules/cm$^2$ of a long wave ultraviolet ray. The above procedure was carried out once a day for 5 consecutive days.

Light Provocation:

Three weeks after the sensitization, the guinea pig was further shorn at the back, where two non-hair sections each of 1.5 cm×1.5 cm were prepared symmetrically with respect to the dorsal median line. Each of the preparations of the Examples and Comparative Examples was applied in an open state onto each section. After shielding one of the sections by aluminum foil, both the sections were irradiated with about 10 Joules/cm$^2$ of a long wave ultraviolet ray from upside.

Evaluation:

Skin photosensitivity was evaluated by comparing the degree of the dermoreactions of the irradiated part and non-irradiated part after 24 hours and 48 hours of the light irradiation in the light provocation. The number of the guinea pigs was 10 in each group and judgement was made according to the criteria in Table 5. The results are shown in Table 6.

TABLE 5

| Erythema and crust formation | Score | Edema formation | Score |
| --- | --- | --- | --- |
| No change | 0 | No change | 0 |
| Very slight erythema | 1 | Very slight to slight edema | 1 |
| Slight erythema | 2 | Medium degree edema | 2 |
| Medium degree to strong erythema | 3 | (Swelled by not less than 1 mm) | 3 |
| Deeply red strong erythema and slight crust formation | 4 | Strong edema (Swelled by 1 mm or more and expanded around) | |

TABLE 6

| Elapsed time after peeling | | Dermal reaction (score) Erythema and crust formation + Edema formation | | | | | | | | Sum (Number) | Positive ratio (%) |
| --- | --- | --- | --- | --- | --- | --- | --- | --- | --- | --- | --- |
| | | 0 | 1 | 2 | 3 | 4 | 5 | 6 | 7 | | |
| 24 Hours | Ex. 2 | 10 | | | | | | | | 10 | 0 |
| | Ex. 6 | 9 | 1 | | | | | | | 10 | 10 |
| | Ex. 8 | 8 | 2 | | | | | | | 10 | 20 |
| | Comp. Ex. 1 | 6 | 3 | 1 | | | | | | 10 | 40 |
| | Comp. Ex. 4 | 5 | 3 | 1 | 1 | | | | | 10 | 50 |
| | Comp. Ex. 5 | 6 | 2 | 2 | | | | | | 10 | 40 |
| 48 Hours | Ex. 2 | 10 | | | | | | | | 10 | 0 |
| | Ex. 6 | 10 | | | | | | | | 10 | 0 |
| | Ex. 8 | 10 | | | | | | | | 10 | 0 |
| | Comp. Ex. 1 | 10 | | | | | | | | 10 | 0 |
| | Comp. Ex. 4 | 9 | 1 | | | | | | | 10 | 10 |
| | Comp. Ex. 5 | 8 | 1 | 1 | | | | | | 10 | 20 |

Table 6 shows that the patches of the Examples are excellent in safety since they caused little or no skin reaction in comparison with the gels and patches of the Comparative Examples.

INDUSTRIAL APPLICABILITY

The patch of the present invention has a backing processed for screening the ultraviolet and, therefore, inhibits the photolysis (mainly caused by ultraviolet sunlight) of medicines contained therein to thereby be able to avoid the fall of medicine content due to the photolysis as well as allergies and poisoning due to the photolysis by-products. Therefore, the patch of the present invention is high in therapeutic effects and dermal safety, and very useful as a medicinal patch in the industry.

What is claimed is:

1. A patch having a base containing ketoprofen as a non-steroidal anti-inflammatory analgesic and a single-layer backing consisting of a woven or non-woven fabric which has been subjected to an ultraviolet-screening processing with at least an organic ultraviolet absorbent, with said backing being the sole backing of the patch.

2. A patch according to claim 1 wherein the ultraviolet-screening processing further includes an inorganic ultraviolet-screening agent.

3. A patch according to claim 2, wherein the inorganic ultraviolet-screening agent is at least one member selected from titanium oxide, zinc oxide, ferric oxide, talc, kaolin, alumina and calcium carbonate.

4. A patch according to claim 3 wherein the backing has a light transmittance of not more than 26% under a condition of an ultraviolet intensity of about 0.14 mW/hr/cm$^2$ and at a temperature of 25° C.

5. A patch according to claim 2 wherein the backing has a light transmittance of not more than 26% under a condition of an ultraviolet intensity of about 0.14 mW/hr/cm$^2$ and at a temperature of 25° C.

6. A patch according to claim 1, wherein the organic ultraviolet absorbent is at least one member selected from benzotriazole derivatives, p-aminobenzoic acid derivatives, anthranilic acid derivatives, salicylic acid derivatives, cinnamic acid derivatives, benzophenone derivatives, coumarinic acid derivatives, cyanoacrylate derivatives and amino acid compounds.

7. A patch according to claim 6 wherein the backing has a light transmittance of not more than 26% under a condition of an ultraviolet intensity of about 0.14 mW/hr/cm$^2$ and at a temperature of 25° C.

8. A patch according to any of claim 1 wherein the backing has a light transmittance of not more than 26% under a condition of an ultraviolet intensity of about 0.14 mW/hr/cm$^2$ and at a temperature of 25° C.

9. A patch according to claim 8 having the base spread on the backing, said base being an adhesive base which further contains 10–50% by mass of a styrene-isoprene-styrene block copolymer, 1–20% by mass of a polyisobutylene, 5–50% by mass of a tackifier and 10–70% by mass of a plasticizer, on the basis of the whole amount of the base.

10. A patch according to claim 1 wherein the content of ketoprofen is 0.1–7.0% by mass based on the whole amount of the base.

11. A patch according to claim 10 having the base spread on the backing, said base being an adhesive base which further contains 10–50% by mass of a styrene-isoprene-styrene block copolymer, 1–20% by mass of a polyisobutylene, 5–50% by mass of a tackifier and 10–70% by mass of a plasticizer, on the basis of the whole amount of the base.

* * * * *